(12) United States Patent
Wada et al.

(10) Patent No.: US 10,520,497 B2
(45) Date of Patent: Dec. 31, 2019

(54) IMMUNOCHROMATOGRAPHIC KIT

(71) Applicant: FUJIFILM Corporation, Tokyo (JP)

(72) Inventors: Atsuhiko Wada, Kanagawa (JP); Akira Wakabayashi, Kanagawa (JP); Keiji Shigesada, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/008,050

(22) Filed: Jun. 14, 2018

(65) Prior Publication Data

US 2018/0292398 A1 Oct. 11, 2018

Related U.S. Application Data

(63) Continuation of application No. PCT/JP2016/005163, filed on Dec. 16, 2016.

(30) Foreign Application Priority Data

Dec. 18, 2015 (JP) ................................ 2015-247351

(51) Int. Cl.
  *G01N 33/543* (2006.01)
  *G01N 33/569* (2006.01)
  *G01N 33/577* (2006.01)

(52) U.S. Cl.
  CPC ......... *G01N 33/543* (2013.01); *G01N 33/569* (2013.01); *G01N 33/577* (2013.01); *B01L 2300/06* (2013.01)

(58) Field of Classification Search
  None
  See application file for complete search history.

(56) References Cited

U.S. PATENT DOCUMENTS

| 6,017,494 A | 1/2000 | Ashihara et al. |
| 6,020,117 A | 2/2000 | Bauer et al. |
| (Continued) | | |

FOREIGN PATENT DOCUMENTS

| JP | H10104236 | 4/1998 |
| JP | 2005061910 | 3/2005 |
| JP | 2006524815 | 11/2006 |
| (Continued) | | |

OTHER PUBLICATIONS

"International Search Report (Form PCT/ISA/210) of PCT/JP2016/005163," dated Feb. 28, 2017, with English translation thereof, pp. 1-5.

(Continued)

*Primary Examiner* — Rebecca L Martinez
(74) *Attorney, Agent, or Firm* — JCIPRNET (57) ABSTRACT

A housing case that includes an inspection strip, a first pot in which a first amplification liquid is sealed, and a second pot in which a second amplification liquid is sealed, includes a lower case, an upper case, and an intermediate member disposed therebetween, in which the upper case includes, on a part facing the first pot, a first protrusive deforming portion that deforms towards a side of the first pot when applied with pressing force from outside, whereby a tearing portion of the intermediate member tears a sheet member of the first pot, and includes, at a part facing the second pot, a second protrusive deforming portion that deforms towards a side of the second pot when applied with pressing force from outside, whereby a sheet member of the second pot is torn.

9 Claims, 4 Drawing Sheets

(56) References Cited

U.S. PATENT DOCUMENTS

2004/0214253 A1 10/2004 Paek et al.
2012/0058465 A1 3/2012 Mori et al.

FOREIGN PATENT DOCUMENTS

| | | |
|---|---|---|
| JP | 2007064829 | 3/2007 |
| JP | 2010230634 | 10/2010 |
| JP | 2011099724 | 5/2011 |
| WO | 8606488 | 11/1986 |
| WO | 2011111108 | 9/2011 |
| WO | 2012170435 | 12/2012 |

OTHER PUBLICATIONS

"Written Opinion of the International Searching Authority (Form PCT/ISA/237) of PCT/JP2016/005163," dated Feb. 28, 2017, with English translation thereof, pp. 1-10.
"International Preliminary Report on Patentability (Form PCT/IPEA/409) of PCT/JP2016/005163," dated Jan. 9, 2018, with English translation thereof, pp. 1-16.
"Search Report of Europe Counterpart Application", dated Sep. 18, 2018, p. 1-p. 6.

IMMUNOCHROMATOGRAPHIC KIT

CROSS-REFERENCE TO RELATED APPLICATIONS

This application is a continuation application of International Application No. PCT/JP2016/005163 filed Dec. 16, 2016, which was published under PCT Article 21(2) in Japanese, and which claims priority under 35 U.S.C. § 119(a) to Japanese Patent Application No. 2015-247351, filed Dec. 18, 2015. The above applications are hereby expressly incorporated by reference, in their entirety, into the present application.

BACKGROUND OF THE INVENTION

1. Field of the Invention

The present invention relates to an immunochromatographic kit, particularly an immunochromatographic kit used to carry out signal amplification operation for enhancing detection sensitivity.

2. Description of the Related Art

Among immunoassay methods, an immunochromatographic method is easy to operate and is capable of performing measurement within a short period of time and thus is generally used as a simple method for detecting test substances.

Competitive responses or sandwich-based responses are widely used as an immune response used in the immunochromatographic method. Among these, the sandwich-based responses are mainstream, and a typical inspection method is as follows.

First, microparticles sensitized by an antibody against an antigen which is a test substance are immobilized as solid-phase microparticles on a chromatographic carrier, or the antibody itself is directly immobilized on the chromatographic carrier, and thus a chromatographic carrier having a reaction site is produced. Alternatively, sensitized labeled microparticles are prepared by sensitizing labeled microparticles with an antibody capable of specifically binding to a test substance.

The sensitized labeled microparticles are then chromatographically moved together with a sample on the chromatographic carrier and in a reaction site on the chromatographic carrier, the sensitized labeled microparticles specifically bind to the immobilized antibody via the antigen which is a test substance. As a result, the sensitized labeled microparticles are trapped at the reaction site. By visually determining the presence or absence or a degree of a signal generated by the sensitized labeled microparticles trapped at the reaction site, it is possible to measure presence or absence or an amount of the test substance in the sample.

In such an immunochromatographic method, a technique for amplifying a detection signal has been proposed in order to avoid a problem of showing a false negative because the test substance is not detected due to low sensitivity despite the test substance being contained. As a method for signal amplification, JP2005-061910A, JP2006-524815A, and the like disclose techniques using enzymes such as alkaline phosphatase and peroxidase as labels. In addition, JP2011-99724A discloses a technique capable of detection with higher sensitivity even in a case where an amount of antigens is small by a technique in which detection is carried out by amplification (silver amplification) using a compound containing silver and a silver ion reducing agent which reacts with a label selected from the group consisting of a metal colloid label and a metal sulfide label.

According to the method for amplifying a detection signal by silver amplification disclosed in JP2011-99724A, detection with significantly high sensitivity becomes possible. In this silver amplification method, it is necessary to supply, to an immunochromatographic carrier, two types of liquids, which are a liquid for catalyzing amplification such as a solution containing a silver ion reducing agent and a liquid for performing amplification such as a solution containing silver ions.

SUMMARY OF THE INVENTION

A device that accommodates the immunochromatographic carrier disclosed in JP2011-99724A is assumed to be set in an analyzer or the like which is operated by a power source so as to perform supply of an amplification liquid by an operation of an external force imparting mechanism or the like provided in the analyzer. Therefore, in a dedicated analyzer operated by a power supply, a defect in which the analyzer cannot be used in a situation where electric infrastructures stop, such as emergency disaster, or in an environment where electricity is not working, may occur.

The present invention has been made in consideration of the above-described circumferences and an object thereof is to provide an immunochromatographic kit which can realize highly sensitive measurement without requiring a dedicated analyzer.

According to the present invention, an immunochromatographic kit for detecting a test substance in a specimen liquid, the kit comprises: an inspection strip including an insoluble carrier that has an inspection region for the test substance, at which the specimen liquid is deployed; a first pot and a second pot each including a surface having a sheet member, a first amplification liquid and a second amplification liquid being sealed, respectively, in the first pot and the second pot in order to amplify a detection signal in the inspection region; and a housing case that includes the inspection strip, the first pot, and the second pot, in which the housing case includes a lower case having an accommodation portion in which the inspection strip is disposed, an upper case joined to the lower case along a peripheral edge thereof, and an intermediate member disposed between the upper case and the lower case, the intermediate member includes a tearing portion that tears the sheet member of the first pot, the tearing portion facing the sheet member of the first pot, and the upper case includes, at a part facing the first pot, a first protrusive deforming portion that deforms towards a side of the first pot when applied with pressing force from outside, whereby the tearing portion of the intermediate member tears the sheet member of the first pot, and the upper case includes, at a part facing the second pot, a second protrusive deforming portion that deforms towards a side of the second pot when applied with pressing force from outside whereby the sheet member of the second pot is torn.

In the immunochromatographic kit according to the present invention, it is preferable that the first protrusive deforming portion is applied with a pressing force so as to move the first pot to a position where the sheet member is torn by the tearing portion of the intermediate member.

In this case, it is preferable that the upper case includes two protrusion portions which project towards the first pot side and that come into contact with the first pot so as to move the first pot in a case in which pressing force is applied to the first protrusive deforming portion.

In the immunochromatographic kit according to the present invention, it is preferable that the first protrusive deforming portion has a centrally symmetrical protruding shape.

In this case, it is preferable that the two protrusion portions are disposed symmetrically with respect to a top of the protruding shape.

In this case, it is preferable that the two protrusion portions are independently formed at inclined surfaces that sandwich the top of the protruding shape therebetween.

In the immunochromatographic kit according to the present invention, in a case where the first protrusive deforming portion has the two protrusion portions, it is preferable that the two protrusion portions are disposed symmetrically with respect to a center of a contact surface of the first pot.

In addition, it is preferable that the two protrusion portions are disposed closer to an end side than a half of a distance from a center to an end of the contact surface of the first pot.

The protrusive deforming portion in the present specification means that the portion has a protruding shape in a case of being seen from the outside of the immunochromatographic kit. Furthermore, the protruding shape means a protruding shape in a case of being seen from the outside.

In the immunochromatographic kit according to the present invention, in a case where the first protrusive deforming portion includes the two protrusion portions described above, the first protrusive deforming portion can be constituted such that distal ends of the two protrusion portions respectively come into contact with the first pot so as to move the first pot while the distal ends are gradually displaced towards the end sides.

In the immunochromatographic kit according to the present invention, it is preferable that a material forming the first protrusive deforming portion has a modulus of elasticity in bending of 50 MPa to 350 MPa.

In addition, it is preferable that a material forming the upper case has a modulus of elasticity in bending of 50 MPa to 350 MPa, and a material forming the lower case has a modulus of elasticity in bending of 500 MPa to 900 MPa.

In the immunochromatographic kit according to the present invention, it is preferable that the upper case is integrally formed with the first protrusive deforming portion and the second protrusive deforming portion by injection molding.

In the immunochromatographic kit of the present invention, the upper case includes, on a part facing the first pot, the first protrusive deforming portion that is deformed towards the first pot side by being applied with pressing force from outside, the tearing portion of the intermediate member tears the sheet member of the first pot, and the upper case includes, at a part facing the second pot, the second protrusive deforming portion that deforms towards a side of the second pot when applied with a pressing force from outside, whereby so that the sheet member of the second pot is torn. The two protrusive deforming portions are applied with a pressing force with a finger or the like of a human so as to be deformed, and the sheet member of the pot can be torn, and thus the amplification liquid can be supplied to the inspection strip. Therefore, an amplification reaction can be performed normally without a dedicated analyzer requiring a power source. Accordingly, the immunochromatographic kit of the present invention is particularly useful in a case of not including a dedicated analyzer, or in a case where a dedicated analyzer cannot be used, such as an emergency or disaster.

DESCRIPTION OF THE PREFERRED EMBODIMENTS

Hereinafter, an embodiment of the present invention will be described using the accompanying drawings, but the present invention is not limited thereto. Meanwhile, in order for better visibility, the reduction scales and the like of individual constitutional elements in the drawings are appropriately changed from actual sizes.

Figure 1:
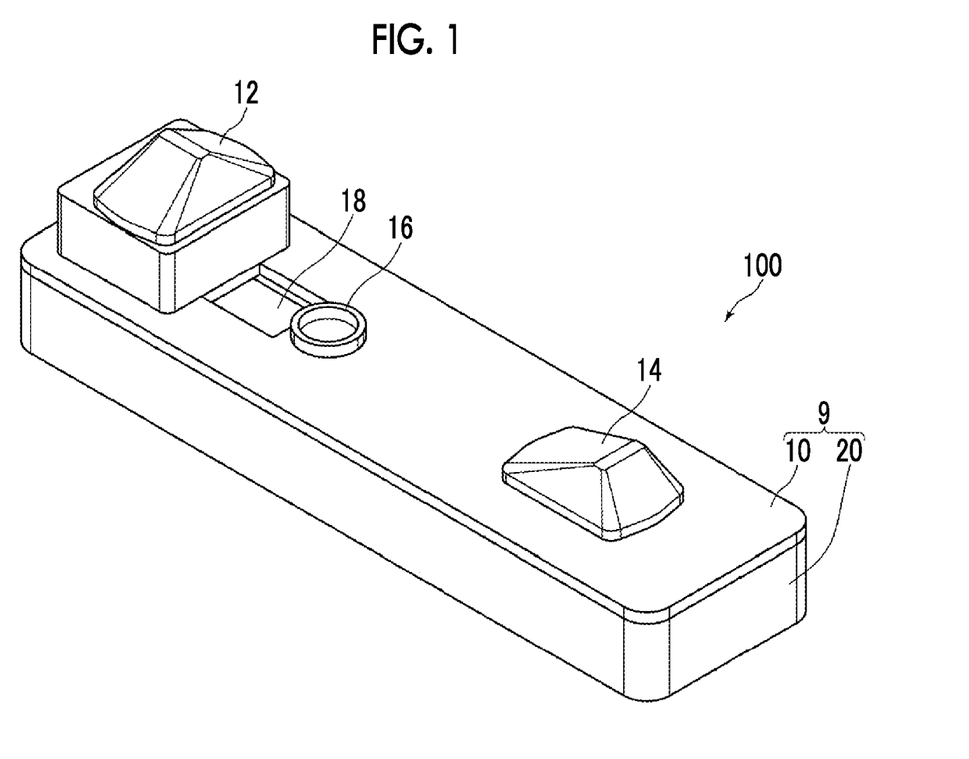
FIG. 1 is a perspective view illustrating an aspect of a first embodiment of an immunochromatographic kit of the present invention.
Figure 2:
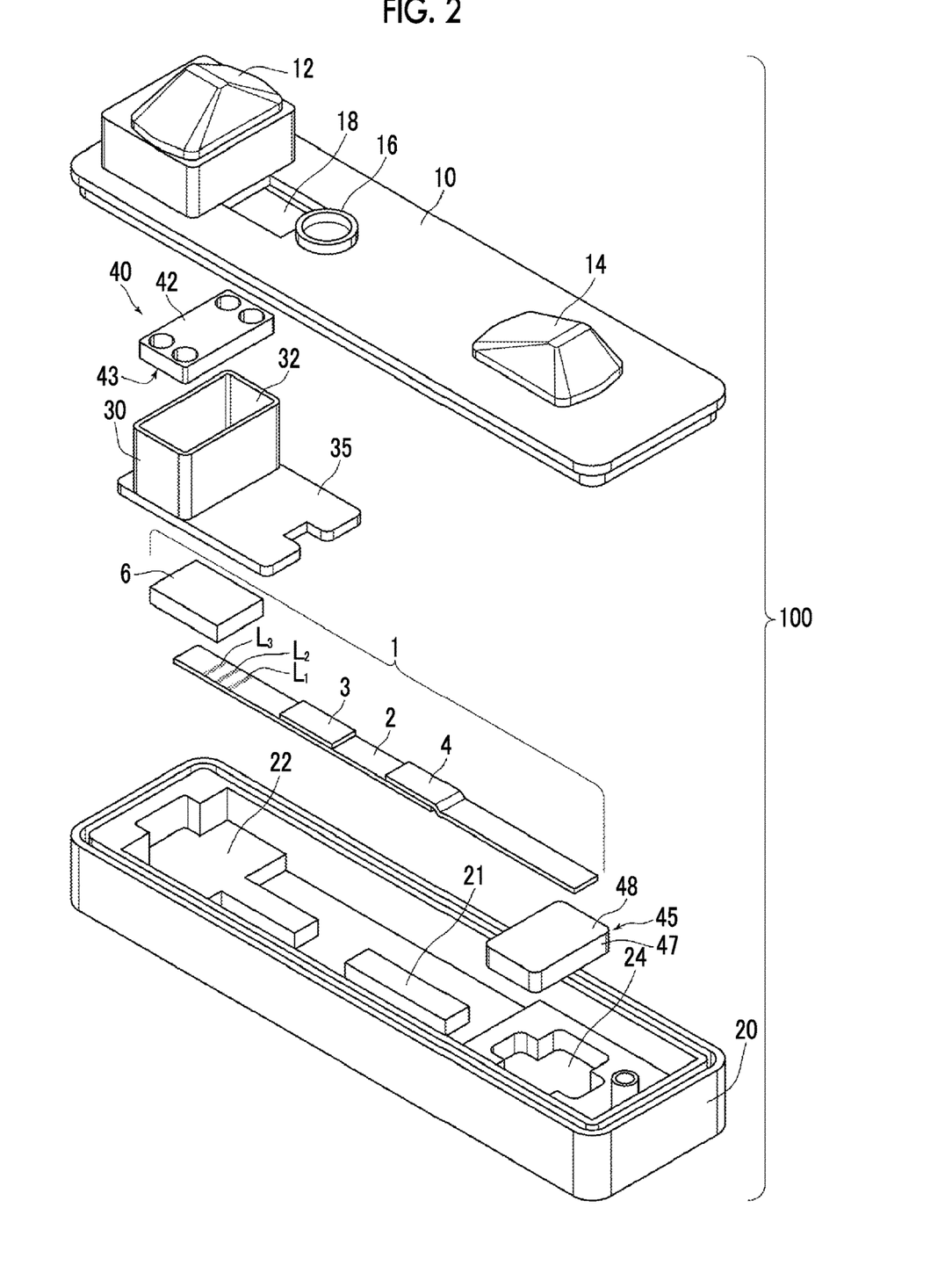
FIG. 2 is an exploded schematic perspective view illustrating an aspect of the first embodiment of the immunochromatographic kit of the present invention.

FIG. 1 is an exploded schematic perspective view illustrating an immunochromatographic kit 100 according to an embodiment of the present invention, and FIG. 2 is an exploded schematic perspective view of the immunochromatographic kit 100 of FIG. 1.

As illustrated in FIG. 1 and FIG. 2, in the immunochromatographic kit 100 of the present embodiment, a housing case 9 includes an inspection strip 1 that has an insoluble carrier 2 having an inspection region for a test substance, at which a specimen liquid is deployed, and a first pot 40 and a second pot 45 which include a surface having a sheet member and in which a first amplification liquid 41 and a second amplification liquid 46 are sealed, respectively, in order to amplify a detection signal in the inspection region. The housing case 9 includes a lower case 20 having an accommodation portion 21 in which the inspection strip 1 is disposed, an upper case 10 joined to the lower case 20 along a peripheral edge, and an intermediate member 30 disposed between the upper case 10 and the lower case 20. In explaining the immunochromatographic kit 100, the upper case side 10 is defined as an upper part and the lower case side 20 is defined as a lower part.

The intermediate member 30 has a first pot accommodation portion 32 which accommodates the first pot 40 and includes on the bottom surface an amplification liquid-filling hole for adding the first amplification liquid 41 dropwise onto the insoluble carrier 2. In addition, a protrusive tearing portion 34 that tears a sheet member 43 is provided at a location facing the sheet member 43 of the first pot 40 in the first pot accommodation portion 32. In the present example, the first pot 40 is disposed above the first pot accommodation portion 32 so that the surface having the sheet member 43 becomes the lower surface, and the tearing portion 34 is provided on the bottom surface of the first pot accommodation portion 32 facing the sheet member 43 (refer to FIG. 3).

In addition, a flow path-forming member 35 is provided so as to extend to a downstream side of the bottom surface of the first pot accommodation portion 32 of the intermediate member 30. The flow path-forming member 35 is disposed to correspond with the positions above an inspection region $L_1$, a confirmation region $L_2$, and an amplification label region $L_3$, and is formed of a transparent material so that these regions $L_1$ to $L_3$ can be visually checked.

The upper case 10 includes, on a part facing the first pot 40, a first protrusive deforming portion 12 that is deformed towards the first pot 40 side by being applied with a pressing force from the outside so as to allow the tearing portion 34 of the intermediate member 30 to tear the sheet member 43 of the first pot 40. In addition, the upper case 10 includes, on a part facing the second pot 45, a second protrusive deforming portion 14 that is deformed towards the second pot 45 side by being applied with a pressing force from the outside so that a sheet member 48 of the second pot 45 is torn.

In addition, a hole 16 for dropwise addition of specimen liquid is provided in the upper case 10, the specimen liquid is added dropwise onto a label-holding pad 3 of the inspection strip 1 from this hole 16. In a case where the location of the label-holding pad 3 is adjusted so that the locations of the hole 16 and the label-holding pad 3 correspond to each other, it becomes possible to reliably spot the specimen liquid onto the label-holding pad 3. In addition, the upper case 10 includes an observation window 18 for visually checking the three regions $L_1$ to $L_3$ at positions corresponding to the flow path-forming member 35 of the intermediate member 30.

In the lower case 20, as an accommodation portion in which the inspection strip 1 is disposed, the insoluble carrier accommodation portion 21 in which the insoluble carrier 2 is mounted is provided, and an absorption pad accommodation portion 22 in which an absorption pad 6 is mounted is provided on the downstream side of the insoluble carrier accommodation portion. In addition, a second pot accommodation portion 24 in which the second pot 45 is accommodated is provided on the upstream side of the insoluble carrier accommodation portion 21.

Figure 3:
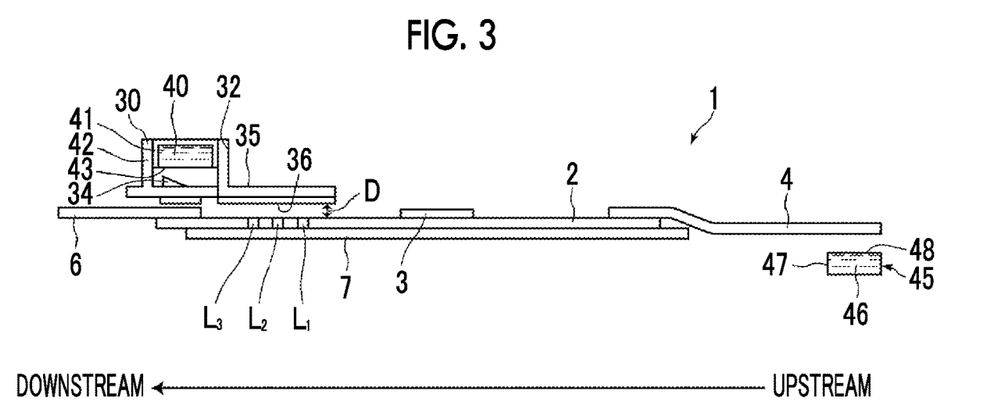
FIG. 3 is a schematic side view illustrating a positional relationship between an inspection strip, and first and second pots.

FIG. 3 is a schematic side view illustrating a positional relationship between the inspection strip 1, the intermediate member 30, and the two pots 40 and 45. As illustrated in FIG. 3, the inspection strip 1 includes the insoluble carrier 2, at which the specimen liquid is deployed, the label-holding pad 3 including a label substance modified with a first substance bondable to a test substance fixed on the insoluble carrier 2, a liquid-sending pad 4 being disposed in contact with one end of the insoluble carrier 2 and sending the second amplification liquid 46 to the insoluble carrier 2, and the absorption pad 6 disposed in contact with the other end of the insoluble carrier 2. The insoluble carrier 2 is fixed to and supported by a back pressure-sensitive adhesion sheet 7. In addition, the insoluble carrier 2 sequentially has the inspection region $L_1$ including a second substance being bonded to the test substance, the confirmation region $L_2$ including a substance bondable to the first substance, and the amplification label region $L_3$ including a substance being reacted with the second amplification liquid from the label-holding pad 3 side between the label-holding pad 3 and the absorption pad 6.

Meanwhile, in the present specification, there are cases in which the insoluble carrier 2 obtained by forming the inspection region $L_1$, the confirmation region $L_2$, and the amplification label region $L_3$ referred to as a chromatographic carrier. In addition, in the present specification, as illustrated in FIG. 3, the liquid-sending pad 4 side is defined as an upstream side and the absorption pad 6 side is defined as a downstream side.

The intermediate member 30 is positioned at the upper portion of a downstream end side of the inspection strip 1 and the first pot 40 is disposed in the first pot accommodation portion 32 of the intermediate member 30 with the sheet member 43 facing downward. The second pot 45 is accommodated below an upstream end of the inspection strip 1 of the lower case 20 with the sheet member 48 facing upward.

As shown in FIG. 3, a gap (clearance) D is formed between a rear surface 36 of the flow path-forming member 35 of the intermediate member 30 and the insoluble carrier 2 of the inspection strip 1. The gap D is preferably within a range of 0.01 mm to 1 mm. In a case where the gap is 0.01 mm or more, the amplification liquid and the like can sufficiently infiltrate, and in a case where the gap is 1 mm or less, capillary force is exerted and the gap between the insoluble carrier 2 and the intermediate member 30 can be uniformly filled with the first amplification liquid 41.

In the first pot 40 enclosing the first amplification liquid 41, for example, a container 42 which is constituted of a resin material and has an opening on one surface is filled with the first amplification liquid 41, and the opening of the container 42 is covered with the tearable sheet member 43 so as to be sealed.

Similarly, in the second pot 45 enclosing the second amplification liquid 46, for example, a container 47 which is constituted of a resin material and has an opening on one surface is filled with the second amplification liquid 46, and the opening of the container 47 is covered with the tearable sheet member 48 so as to be sealed.

As the tearable sheet members 43 and 48 in the first pot 40 and the second pot 45, laminate films such as aluminum foils and aluminum sheets are suitability used. The term "tear" refers to a state in which the sheet does not regenerate after being torn.

The two protrusive deforming portions 12 and 14 of the upper case will be described in detail.

Figure 4:
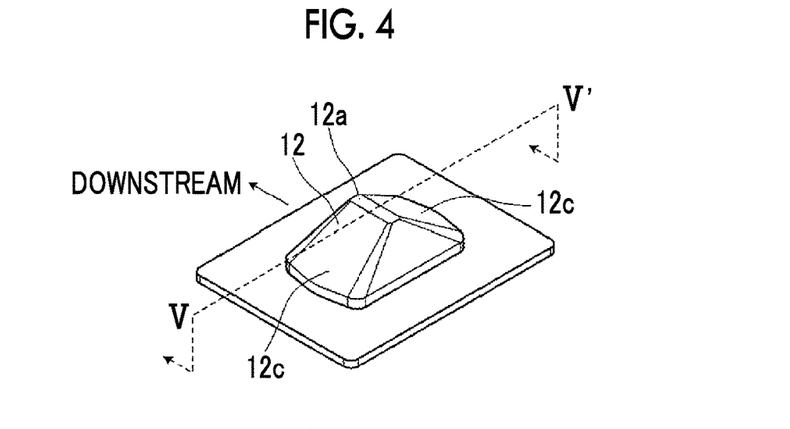
FIG. 4 is a perspective view illustrating a first protrusive deforming portion provided on an upper case of the immunochromatographic kit shown in FIG. 1.
Figure 5:
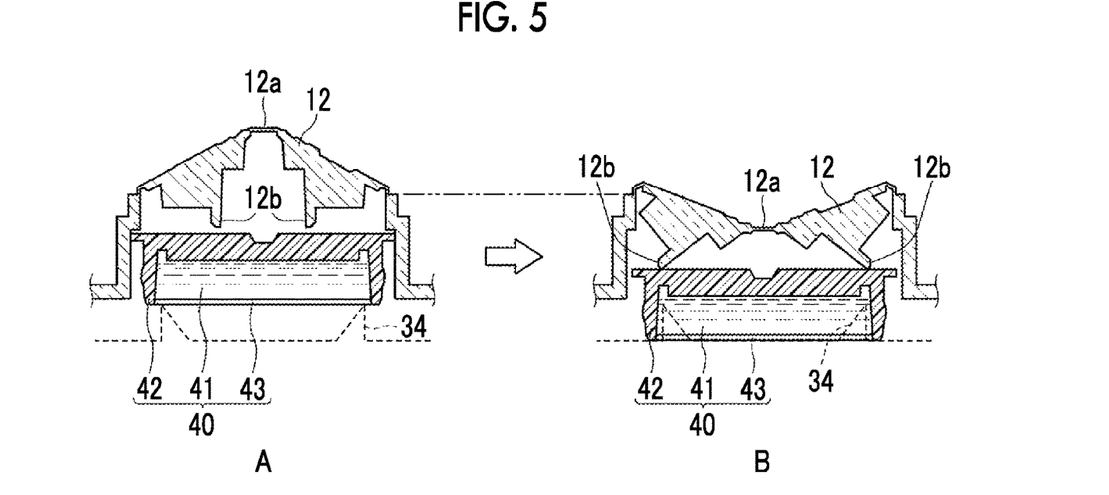
FIG. 5 is a cross-sectional view of cut portions taken along a line V-V' before and after deformation of the first protrusive deforming portion shown in FIG. 4.

FIG. 4 is a perspective view illustrating the first protrusive deforming portion 12, FIG. 5 is a cross-sectional view of cut portions taken along a line V-V' of FIG. 4, A of FIG. 5 is a view illustrating the first protrusive deforming portion 12 before and after deformation, and B of FIG. 5 is a view illustrating a state after the deformation and a positional relationship with the first pot 40.

The first protrusive deforming portion 12 is applied with pressing force from the outside so as to move the first pot 40 to a position where the sheet member 43 is torn by the tearing portion 34 of the intermediate member 30. Specifically, the first protrusive deforming portion 12 is constituted to be pressed toward a lower portion by being pressed down with a finger or the like. The first protrusive deforming portion 12 is deformed and protrude downward (in a concave shape in a case of being seen from the outside) so as to move the first pot 40 towards the tearing portion 34 to a position where the sheet member 43 of the first pot 40 is torn by the tearing portion 34 in the first pot accommodation portion 32 of the intermediate member 30. Therefore, tearing portion 34 tears through the sheet member 43 of the first pot 40, and it becomes possible to supply the first amplification liquid 41 to the outside. The first amplification liquid 41 is added dropwise to the upper portion of the insoluble carrier 2 from the amplification liquid-filling hole that is provided on the bottom surface of the first pot accommodation portion 32 in the intermediate member 30, and it becomes possible to supply the first amplification liquid 41 to the inspection region $L_1$, the confirmation region $L_2$, and the amplification label region $L_3$ on the insoluble carrier. Meanwhile, at this case, the first amplification liquid 41 added dropwise to the upper portion of the insoluble carrier 2 from the amplification liquid-filling hole fills the gap between the intermediate member 30 and the insoluble carrier 2, is supplied to the above of the inspection region $L_1$, the confirmation region $L_2$, and the amplification label region $L_3$ through the gap, and gradually permeates into the insoluble carrier 2.

As shown in FIG. 5, the first protrusive deforming portion 12 has two protrusion portions 12b projecting towards the first pot 40 side at a position facing the first pot 40. In a case where the first protrusive deforming portion 12 is applied with a pressing force so as to deformed, the two protrusion portions 12b are constituted so as to come into contact with the first pot 40 and thus to move the first pot 40.

The first protrusive deforming portion 12 has a centrally symmetrical protruding shape, and the two protrusion portions 12b are disposed symmetrically with respect to a top 12a of the protruding shape and are independently formed below (rear surface) an inclined surface 12c that sandwiches the top 12a.

As shown in A of FIG. 5, before the deformation, the first protrusive deforming portion 12 is formed on the upper case 10 such that the two protrusion portions 12b comes to a position symmetrical to a center of a contact surface of the first pot 40. The tearing portion 34 of the intermediate member 30 is positioned below the sheet member 43 of the first pot 40 as indicated by broken lines of FIG. 5. In a case where the first protrusive deforming portion 12 is applied with a pressing force so as to be deformed, the two protrusion portions 12b are disposed such that distal ends of the two protrusion portions 12b respectively come into contact with the first pot 40 so as to move the first pot 40 while the distal ends being respectively gradually displaced towards the end sides of the first pot 40. As shown in B of FIG. 5, after the deformation of the protrusive deforming portion 12, the gap between the two protrusion portions 12b expands, and the distal ends of the two protrusion portions 12b come to a position closer to an end side than a half of a distance from the center to an end of the contact surface of the first pot 40. In the present embodiment, the two protrusion portions 12b are provided independently, the two protrusion portions 12b have the gap therebetween (the rear surface of the top 12a), the protrusive deforming portion 12 is formed of a flexible material, and therefore the first pot 40 is pushed down while the two protrusion portions 12b are greatly expanded.

A shape or the placement of the two protrusion portions 12b are not limited to the above embodiment, and for example, before the deformation, the two protrusion portions 12b may be provided at positions closer to the end side than a half of a distance from the center to the end of the contact surface of the first pot 40.

In the first protrusive deforming portion 12 for moving the first pot 40, it is possible to evenly push the first pot 40 at two places because there are two protrusion portions 12b, and therefore the first pot 40 can be moved in parallel.

The first protrusive deforming portion 12 is easily deformed by being pushed with a finger or the like, and the first protrusive deforming portion 12 becomes downwardly a protrusion shape (concave shape). A configuration in which the concave shape does not return after this pressing and thus it is possible to maintain the state in which the first pot 40 is pressed, is preferable. The first protrusive deforming portion 12 is configured to press the top 12a, but similarly, the deformation is also possible by pressing the inclined surface of the protruding shape due to the elasticity of the protrusive deforming portion 12.

Figure 6:
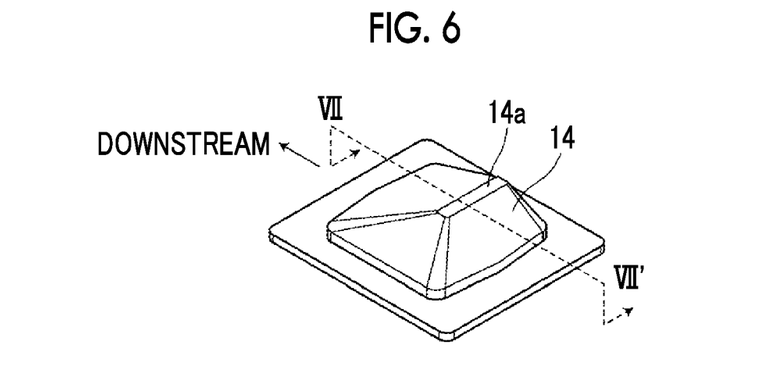
FIG. 6 is a perspective view illustrating a second protrusive deforming portion provided on the upper case of the immunochromatographic kit shown in FIG. 1.
Figure 7:
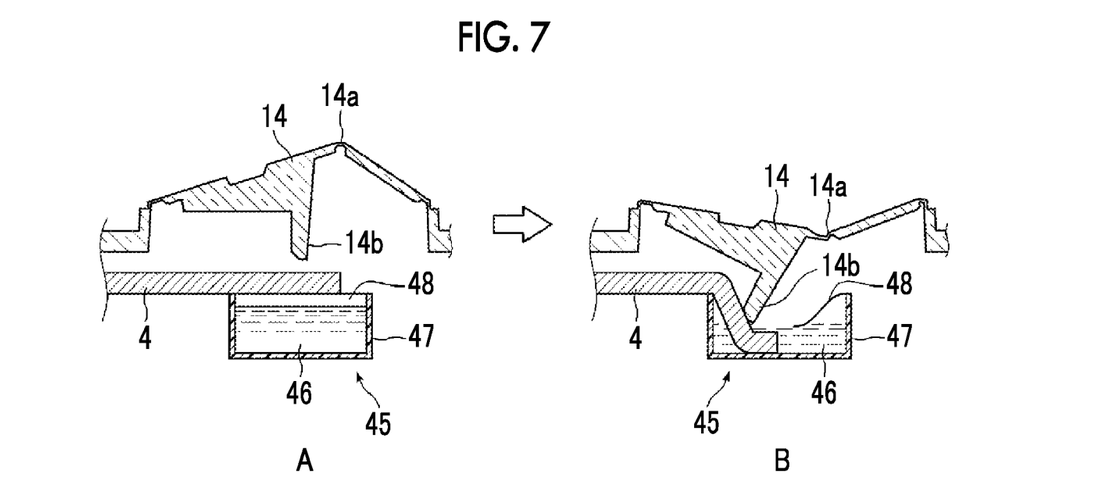
FIG. 7 is a cross-sectional view of cut portions taken along a line VII-VII' before and after deformation of the second protrusive deforming portion shown in FIG. 6.

FIG. 6 is a perspective view illustrating the second protrusive deforming portion 14, FIG. 7 is a cross-sectional view of cut portions taken along a line VII-VII' of FIG. 6, A of FIG. 7 is a view illustrating the second protrusive deforming portion 14 before and after deformation, and B of FIG. 7 is a view illustrating a state after the deformation and a positional relationship with the second pot 45.

The second protrusive deforming portion 14 is applied with a pressing force, and therefore the sheet member 48 of the second pot 45 is torn. As shown in A of FIG. 7, the second protrusive deforming portion 14 has one protrusion portion 14b projecting towards the second pot 45 at a position facing the second pot 45. In addition, the liquid-sending pad 4 of the inspection strip 1 is disposed between the second pot 45 and the protrusion portion 14b. The second protrusive deforming portion 14 is applied with a pressing force is applied so as to protrude toward the second pot 45 side, that is, so as to be deformed into a concave shape in a case of being seen from the outside, and as shown in B of FIG. 7, the protrusion portion 14b comes into contact with a surface of the liquid-sending pad 4 so that the sheet member 48 of the second pot 45 is torn up through the liquid-sending pad 4 is pressed into the second pot 45. As shown in FIG. 7, the second protrusive deforming portion 14 is constituted to have a protruding shape having a top 14a on a slightly upstream side in a cross section along the upstream and downstream directions, and such that the protrusion portion 14b is inclined toward the downstream side so as to tear through the sheet member 48 at the time of deformation.

By this operation, the liquid-sending pad 4 is immersed into the second amplification liquid 46 in the second pot 45, and the second amplification liquid 46 can permeate through the liquid-sending pad 4 by capillarity so as to be supplied to the insoluble carrier 2.

The second protrusive deforming portion 14 also is easily deformed by being pushed with a finger or the like so as to become a concave shape. A configuration in which the concave shape does not return after this pressing and thus it is possible to maintain the state in which the second pot 45 is pressed into the liquid-sending pad 4, is preferable.

The present invention is to realize highly sensitive analysis by deforming the first and second protrusive deforming portions and supplying the amplification liquid without using a device connected to a power source, and therefore in one embodiment, an aspect in which the deformation is performed by a person's hand is presumed. Therefore, a design in which the amplification liquid does not leak to the outside by mistake is preferable, and it is preferable that the first and second protrusive deforming portions 12 and 14 provided in the upper case 10 are integrally formed so as not to have a gap between the other portions of the upper case 10. It is preferable that the protrusive deforming portions 12 and 14 are produced with an extendable material so as to be joined with the other portions of the upper case 10 in a sealed state. The first and second protrusive deforming portions 12 and 14 and the other portions of the upper case 10 may be separately produced and then joined to each other, it is preferable that by injection molding, as a part of the upper case 10, the first and second protrusive deforming portions 12 and 14 are integrally molded as a single continuous member having no joining part.

It is necessary that the first and second protrusive deforming portions 12 and 14 have flexibility at which the deformation can be easily performed by a human finger or the like. A modulus of elasticity in bending of a material forming the protrusive deforming portions 12 and 14 is preferably 50 MPa to 350 MPa, and more preferably 70 MPa to 150 MPa.

In addition, in a case where the upper case 10 and the lower case 20 are merely fitted to each other in a case of combining the upper case 10 and the lower case 20, there is a case where the liquid leaks from the gap, and therefore it is preferable that fitting portions of the upper case 10 and the lower case 20 are also bonded in a sealed state.

As a method for bonding the upper case 10 and the lower case 20, it is preferable to use an ultrasonic welding method. In general, it is known that ultrasonic welding is difficult to weld unless members to be welded are made of the same material, and the combination of the upper case and the lower case is preferably polyethylene/polyethylene, polypropylene/polypropylene, or ABS (acrylonitrile-butadiene-styrene copolymer)/ABS.

In a case where the protrusive deforming portions 12 and 14 are integrally formed on the upper case 10, it is necessary that a material forming the upper case 10 has flexibility. On the other hand, the lower case 20 is preferably rigid so as to fix the inspection strip 1 and the second pot 45. Specifically, a modulus of elasticity in bending of a material forming the upper case 10 is preferably 50 MPa to 350 MPa, and more preferably 70 MPa to 150 MPa. A modulus of elasticity in bending of a material forming the lower case 20 is preferably 500 MPa to 900 MPa, and more preferably 650 MPa to 750 MPa.

The modulus of elasticity in bending is a value calculated from Equation (1) as follows in an environment of a temperature of 20° C. according to a measurement method of the ISO 178 standard.

In regard to the material for measuring the modulus of elasticity in bending, a test piece in the form of a plate having a width b (mm) and a thickness h (mm) is prepared and the test piece is supported by two fulcrum points with a distance between the fulcrum points set to L (mm). A load of F (N) is applied to a center between the fulcrum points and a degree of deflection (mm) is measured in a direction in which the load is applied. A deflection-load curve is created with deflection S (mm) on a horizontal axis and load F (N) on a vertical axis. A tangent line at the origin point of this curve is obtained, an inclination (($\Delta F/\Delta S$) in a case where an amount of change in load $\Delta F$ (N) and an amount of change in deflection $\Delta S$ (mm)) is calculated, and therefore a modulus of elasticity in bending E (MPa) can be calculated using the following equation.

Modulus of elasticity in bending
$$E=(L^3/(4bh^3))\times(\Delta F/\Delta S) \quad \text{Equation (1)}$$

Accordingly, the combination of the upper case and the lower case is most preferably a combination of polypropylene/polypropylene containing a softening agent. The softening agent to be used for the polypropylene containing a softening agent is preferably an olefinic elastomer, and a concentration of the olefinic elastomer with respect to the polypropylene is preferably 20% by mass to 60% by mass and particularly preferably 40% by mass to 55% by mass. Specific examples of the softening agent include TAFTHREN (registered trademark) manufactured by Sumitomo Chemical Co., Ltd.

The immunochromatographic kit of the present invention may include two or more protrusive deforming portions, and in a case where there are three or more kinds of solutions to be supplied to the inspection strip, the immunochromatographic kit may include three or more protrusive deforming portions.

As the insoluble carrier 2, it is possible to use, for example, a nitrocellulose membrane or the like. In addition, the back pressure-sensitive adhesion sheet 7 to which the insoluble carrier 2 is fixed is a sheet-like base material in which a surface to which the insoluble carrier 2 is attached is a pressure-sensitive adhesive surface.

The label-holding pad 3 is fixed to a central portion in a longitudinal direction, of the insoluble carrier 2. As the label substance, it is possible to use, for example, a gold colloid having a diameter of 50 nm (EM. GC50 manufactured by Boston Biomedical Inc.). In a case where a surface of the label substance is modified with a substance being bonded to a test substance, it is possible to form bodies bonded to the test substance.

The label substance is not limited to what has been described above, metal sulfides that can be used in ordinary chromatography, coloring particles that are used in immune agglutination, and the like can be used, and particularly, metal colloids are preferred. Examples of the metal colloids include gold colloids, silver colloids, platinum colloids, iron colloids, aluminum hydroxide colloids, complex colloids thereof, and the like. Particularly, at appropriate particle diameters, gold colloids and silver colloids are preferred because they show red and yellow, respectively, and among these, gold colloids are most preferred.

The inspection strip 1 is positioned such that a position of the hole 16 for dropwise addition of specimen liquid of the upper case 10 corresponds to a position of the label-holding pad 3.

The inspection region $L_1$ is a label substance supplement region in which the second substance being bonded to the test substance is included and the label substance bonded to the test substance is supplemented through the test substance. For example, in a case in which it is intended to detect influenza A-type viruses or biomarkers thereof as a test substance, for example, an aspect in which the inspection region $L_1$ is constituted of antibody immobilization lines in which anti-influenza A-type monoclonal antibodies (Anti-Influenza A SPTN-5 7307, manufactured by Medix Biochemica) are linearly immobilized by means of physical adsorption is preferred.

In a case where a test substance and a complex body to which the label substance is bonded through the first substance arrive at this inspection region $L_1$, the second substance and the test substance are uniquely bonded to each other, and the label substance is supplemented through the test substance and the first substance. Meanwhile, the label substance that does not constitute the complex body with the test substance is not supplemented to the inspection region $L_1$ and simply passes through.

The confirmation region $L_2$ is a region which includes substances bondable to the first substance and is intended to confirm the completion of the deployment of the specimen liquid from the supplement of the label substance through the first substance which has been deployed into the insoluble carrier 2 from the label-holding pad 3 together with the specimen liquid and has passed through the inspection region $L_1$. For example, in a case in which it is intended to detect influenza A-type viruses or biomarkers thereof as a test substance, for example, an aspect in which anti-mouse IgG antibodies (anti-mouse IgG (H+L), rabbit F(ab')2, and Product No. 566-70621 manufactured by Wako Pure Chemical Industries, Ltd.) are linearly immobilized by means of physical adsorption is preferred.

The amplification label region $L_3$ is a region which includes a substance being reacted with the second amplification liquid 46, is reacted with the second amplification liquid 46 and thus produces or changes color, thereby indicating the spread of the second amplification liquid 46 to the region, and serves as an index of timing for the dropwise addition of the first amplification liquid 41. For example, in a case in which a mixed aqueous solution of an aqueous solution of iron nitrate and citric acid (038-06925 manufactured by Wako Pure Chemical Industries, Ltd.) is used as the second amplification liquid 46, an aspect in which the amplification label region $L_3$ is constituted of coloring reagent immobilization lines in which bromocresol green (manufactured by Wako Pure Chemical Industries, Ltd.) is linearly immobilized is preferred. In this case, in a case where the second amplification liquid 46 arrives at the amplification label region $L_3$, the color of the region $L_3$ changes from green to orange. This color change can be considered as an index indicating that the inspection region $L_1$ and the confirmation region $L_2$ are sufficiently wetted with the second amplification liquid 46.

As a method for amplifying the signals of metal-based label substances such as metal colloids, it is preferable to use a method in which silver ions and a reducing agent for the silver ions are brought into contact with a label substance, the silver ions are reduced by the reducing agent so as to generate silver particles, and the silver particles deposit on the label substance using the label substance as a nucleus, thereby amplifying signals using the label substance (hereinafter, silver amplification).

In order to realize the silver amplification, a solution containing silver ions may be used as the first amplification liquid 41, and a reducing agent solution containing a reducing agent for silver ions may be used as the second amplification liquid 46.

(First Amplification Liquid)

A solution containing silver ions used as the first amplification liquid 41 is preferably a solution in which a silver ion-containing compound is dissolved in a solvent. As the silver ion-containing compound, it is possible to use organic silver salts, inorganic silver salts, or silver complexes. Inorganic silver salts or silver complexes are preferred. As the inorganic silver salts, it is possible to use silver ion-containing compounds having a high solubility in solvents such as water, and examples thereof include silver nitrate, silver acetate, silver lactate, silver butyrate, silver thiosulfate, and the like. Silver nitrate is particularly preferred. The silver complexes are preferably silver complexes coordinated with ligands having a water-soluble group such as a hydroxyl group or a sulfone group, and examples thereof include silver hydroxythioether and the like.

(Second Amplification Liquid)

As a reducing agent used in the reducing agent solution containing the reducing agent capable of reducing silver ions used as the second amplification liquid 46, it is possible to use any of an inorganic material, an organic material, or a mixture thereof as long as it is a material capable of reducing silver ions to silver. Preferred examples of inorganic reducing agents include reducing metal salts and reducing metal complexes which are capable of changing the atomic value with metal ions such as $Fe^{2+}$, $V^{2+}$, or $Ti^{3+}$. In a case in which an inorganic reducing agent is used, it is necessary to remove or detoxify oxidized ions by complexing or reducing the oxidized ions. For example, in a system in which $Fe^{2+}$ is used as the reducing agent, a complex of $Fe^{3+}$, which is an oxide, is formed using citric acid or EDTA (ethylenediaminetetraacetic acid), and therefore detoxification is possible. In the present system, such an inorganic reducing agent is preferably used, and a metal salt of $Fe^{2+}$ is more preferred.

In addition, a developing agent used in a light-sensitive silver halide photographic material of a wet type (such as methyl gallate, hydroquinone, substituted hydroquinone, 3-pyrazolidones, p-aminophenols, p-phenylenediamines, hindered phenols, amidoximes, azines, catechols, pyrogallols, ascorbic acid (or derivatives thereof), and leuco dyes), and other materials obvious to those skilled in the art of the field of the present invention, such as a material disclosed in U.S. Pat. No. 6,020,117 A can also be used.

As the reducing agent, an ascorbic acid reducing agent is also preferable. Useful ascorbic acid reducing agents include ascorbic acid and analogs thereof, and isomers and derivatives thereof. Preferred examples thereof include D- or L-ascorbic acid and sugar derivatives thereof (such as γ-lactoascorbic acid, glucoascorbic acid, fucoascorbic acid, glucoheptoascorbic acid, and maltoascorbic acid), a sodium salt of ascorbic acid, a potassium salt of ascorbic acid, isoascorbic acid (or L-erythroascorbic acid), a salt thereof (such as alkali metal salt, ammonium salt, or a salt known in the technical field), ascorbic acid of the enol type, ascorbic acid of the enaminol type, ascorbic acid of the thioenol type, and the like. Particularly preferable examples thereof include D-, L-, or DL-ascorbic acid (and an alkali metal salt thereof) or isoascorbic acid (or an alkali metal salt thereof), and a sodium salt is a preferable salt. If necessary, a mixture of these reducing agents can be used.

In the present embodiment, the first protrusive deforming portion 12 moves the first pot 40 toward the tearing portion 34 provided in the intermediate member 30, but it is enough that as long as the first protrusive deforming portion 12 has a configuration in which along with the deformation thereof, the sheet member 43 of the first pot 40 is torn up by the tearing portion 34.

A configuration of the first pot 40 and the first pot accommodation portion 32 accommodating the first pot 40 are not limited to the configuration of the present embodiment as long as it is a configuration in which the sheet member 43 of the first pot 40 is torn up and it is possible to add dropwise the first amplification liquid 41 flowing out from the first pot 40 onto the insoluble carrier 2 from the amplification liquid-filling hole on the bottom surface of the first pot accommodation portion 32.

In addition, it is preferable that there are two or more protrusion portions of the first protrusive deforming portion in terms of moving the first pot 40 in parallel without incline. The first protrusive deforming portion may have an aspect in which a single protrusion portion has the same shape as that of the second protrusive deforming portion in the above embodiment. The protrusive deforming portion having the same shape as the second protrusive deforming portion may be used as the first protrusive deforming portion for moving the first pot 40.

Figure 8:
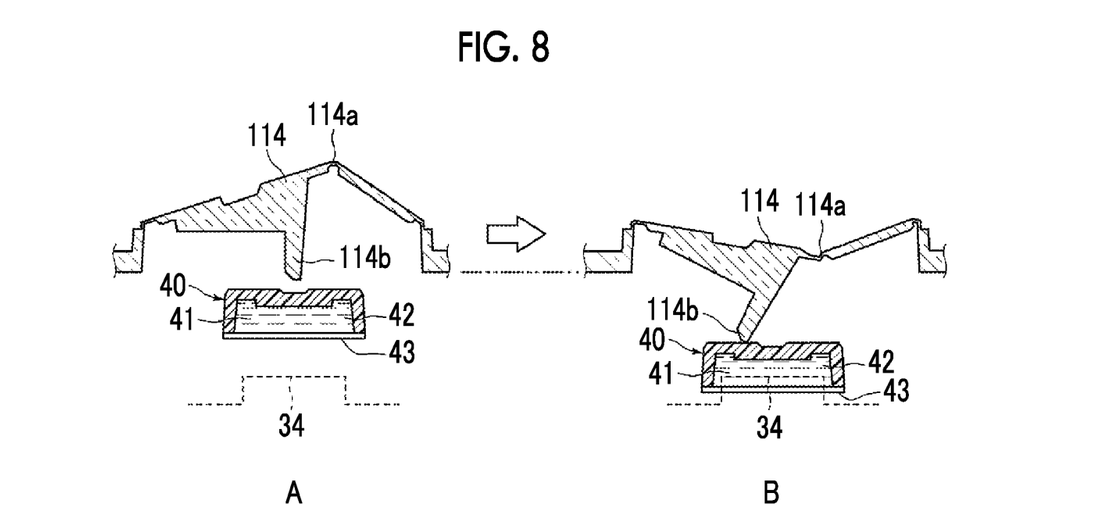
FIG. 8 is a cross-sectional view of cut portions before and after deformation of a protrusive deforming portion of a design change example.

Similarly to FIG. 7, FIG. 8 is a cross-sectional view of cut portions illustrating an aspect of a case in which a deforming portion 114 having the same shape as the second protrusive deforming portion is used for moving the first pot 40.

As shown in A of FIG. 8, before deformation, the first pot 40 is disposed below a protrusion portion 114*b* of the protrusive deforming portion 114. In addition, the tearing portion 34 of the intermediate member 30 is positioned below the first pot 40. By depressing down a top 114*a* of the protrusive deforming portion 114, the protrusion portion 114b is pressed and reaches the upper surface of the first pot 40 so as to press down the first pot 40. As a result, the tearing portion 34 tears through the sheet member 43 of the first pot 40, and the first amplification liquid 41 sealed in the first pot 40 flows out from the first pot so as to be supplied to the inspection strip 1.

In this manner, the pot can be moved even with only one protrusion portion provided to the protrusive deforming portion 114.

Meanwhile, the immunochromatographic kit of the present invention may include a set or a part thereof which is necessary for inspection such as a pot including a test body extraction liquid including an assistant chemical assisting the extraction of test bodies or a pot including a test body dilution liquid, a drying agent or a deoxidizer helping the storage of the kit, attached documents such as manuals, and test body-collecting tools such as ear sticks.

The use of the immunochromatographic kit enables accurate inspection with this kit alone without using exclusive analyzers.

<Immunochromatographic Inspection Method>

An immunochromatographic inspection method using the immunochromatographic kit 100 will be simply described.

The specimen liquid is added dropwise onto the label-holding pad 3 from the hole 16 for dropwise addition of specimen liquid. In a case in which the test substance is included in the specimen liquid, the test substance and the first substance are bonded to each other in the label-holding pad 3, whereby a complex body of the test substance and the label substance is formed through the first substance, and the complex body is spread toward the absorption pad 6 side together with the specimen liquid due to the suctioning force of the absorption pad 6 and capillarity. At the same time as or after the dropwise addition of the specimen liquid, the second protrusive deforming portion 14 is pressed down, the liquid-sending pad 4 is displaced, the sheet member 48 of the second pot 45 is torn up, the second amplification liquid 46 penetrates through the liquid-sending pad 4, and therefore the second amplification liquid 46 is sent to the insoluble carrier 2. Meanwhile, a timing of pressing down the second protrusive deforming portion 14 is preferably within 30 seconds or shorter from the dropwise addition of the specimen liquid and a timing immediately after the dropwise addition of the specimen liquid is particularly preferable.

The complex body arriving at the inspection region $L_1$ is bonded to the second substance in the inspection region $L_1$ so as to be trapped. In addition, the first substance that is not bonded to the test substance passes through the inspection region $L_1$, arrives at the confirmation region $L_2$, is bonded to a substance being bonded to the first substance in the confirmation region $L_2$, and is trapped.

The second amplification liquid 46 arrives at the amplification label region $L_3$ via the inspection region $L_1$ and the confirmation region $L_2$. At this time, the amplification label region $L_3$ discolors, whereby it is possible to visually recognize the arrival of the second amplification liquid 46 at the amplification label region $L_3$. After the discoloration of the amplification label region $L_3$ is confirmed, the first protrusive deforming portion 12 is pressed down and the first amplification liquid 41 is supplied to the insoluble carrier 2.

After the supply of the first amplification liquid 41 to the insoluble carrier 2, it was waited until the completion of the reaction, and the discoloration in the inspection region $L_1$ and the confirmation region $L_2$ is confirmed through the observation window 18. The presence or absence of the test substance and the concentration thereof can be confirmed from the discoloration of the inspection region $L_1$, and whether or not inspection for measuring the test substance is succeeded can be confirmed from the discoloration of the confirmation region $L_2$. Discoloration in the inspection region $L_1$ and the confirmation region $L_2$ is caused by amplifying the signals of the label, and highly sensitive inspection can be carried out.

EXAMPLES

Hereinafter, examples and comparative examples of the immunochromatographic kit of the present invention will be described.

Immunochromatographic kits of the examples and the comparative examples are immunochromatographic kits for influenza virus antigen detection for detecting influenza virus antigens as a test substance.

(1) Production of Immunochromatographic Kit (1-1) Production of Anti-influenza A-type Antibody-Modified Gold Colloid as Label Substance Modified with First Substance Bondable to Test Substance 1 mL of 50 mmol/L of $KH_2PO_4$ buffer (pH 7.5) was added to 9 mL of a solution (Product No.: EM. GC50, manufactured by Boston Biomedical Inc.) containing gold colloid having a diameter of 50 nm so as to adjust a pH, and then 1 mL of a solution containing 160 μg/mL of an anti-influenza A-type monoclonal antibody (Anti-Influenza A SPTN-5 7307, manufactured by Medix Biochemica) was added thereto and stirred for 10 minutes. Thereafter, after the solution mixture was left to stand for ten minutes, 550 μL of an aqueous solution containing polyethylene glycol (PEG; weight-average molecular weight (Mw.): 20,000, Product No. 168-11285, manufactured by Wako Pure Chemical Industries, Ltd.) of 1% by mass was added to and stirred with the solution mixture for 10 minutes, and subsequently, 1.1 mL of an aqueous solution of bovine serum albumin (BSA) of 10% by mass; FractionV, Product No.: A-7906, manufactured by Sigma-Aldrich Co. LLC.) was added to and stirred with the solution mixture for 10 minutes. This solution was centrifuged for 30 minutes under conditions of 8000 μg at 4° C. using a centrifugal separator (himacCF16RX, manufactured by Hitachi Ltd.). The supernatant liquid was removed by 1 mL left at the bottom of the container, and the gold colloid contained in the 1 mL solution left at the bottom of the container was re-dispersed by an ultrasonic washer. After that, the gold colloid was dispersed in 20 mL of a gold colloid preservative solution (20 mmol/L Tris-HCl (Tris hydrochloric acid) buffer (pH 8.2), 0.05% PEG (Mw. 20,000), 150 mmol/L NaCl, 1% BSA) and was again centrifuged under the same conditions using the same centrifugal separator, and then the supernatant was removed, followed by ultrasonic dispersion and dispersion in gold colloid preservation solution, and therefore an antibody-modified gold colloid (50 nm) solution was obtained.

(1-2) Production of Anti-influenza A-type Antibody-modified Gold Colloid-holding Pad as Label-holding Pad The influenza A-type antibody-modified gold colloid produced in (1-1) was diluted with water so that the concentration of the Tris-HCl buffer (pH: 8.2) reached 20 mmol/L, the concentration of PEG (Mw. 20,000) reached 0.05% by mass, the concentration of sucrose reached 5% by mass, and the optical density of the gold colloid at 520 nm reached 0.1 when the light wavelength was set to 10 mm, thereby producing a gold colloid coating fluid. This coating fluid was uniformly applied onto 12 mm×300 mm-cut glass fiber pads (Glass Fiber Conjugate Pad, manufactured by EMD Millipore Corporation) at 0.8 mL per pad and was dried at reduced pressure for 24 hours, thereby obtaining an influenza A-type antibody-modified gold colloid-holding pad.

(1-3) Production of Chromatographic Carrier

As the insoluble carrier, a 60 mm×300 mm-cut nitrocellulose membrane (with a plastic backing, HiFlow Plus HF135 (capillary flow rate=135 sec/cm), manufactured by EMD Millipore Corporation) was used, and the inspection region, the confirmation region, and the amplification label region were formed on this membrane using a method as described below, thereby producing a chromatographic carrier.

An anti-influenza A-type monoclonal antibody (Anti-Influenza A SPTN-5 7307, manufactured by Medix Biochemica) solution prepared so as to be 1.5 mg/mL was applied in a line shape at a position 15 mm from the downstream side of the 60 mm short side of the nitrocellulose membrane, thereby producing the inspection region. Furthermore, an anti-mouse IgG antibody (anti-mouse IgG (H+L), rabbit F(ab')2, Product No. 566-70621, manufactured by Wako Pure Chemical Industries, Ltd.) solution produced so as to be 0.2 mg/mL was applied in a line shape at a position 11 mm from the downstream side of the 60 mm short side, thereby producing the confirmation region. Furthermore, similarly, bromocresol green (manufactured by Wako Pure Chemical Industries, Ltd.) produced so as to be 30 mmol/L was applied in a line shape at a position 9 mm from the downstream side of the 60 mm short side, thereby producing the amplification label region. After the application of the respective components, the nitrocellulose membrane was dried at 50° C. for 30 minutes using a warm air-type dryer. After the completion of the drying, the nitrocellulose membrane dried as described above was immersed in a vat in which 500 mL of a blocking liquid (50 mmol/L of a boric acid buffer (pH: 8.5) containing 0.5% by mass casein (derived from milk, Product No. 030-01505, manufactured by Wako Pure Chemical Industries, Ltd.)) was added, and left to stand for 30 minutes. Thereafter, the nitrocellulose membrane was taken out, and the nitrocellulose membrane was immersed into 500 mL of a washing and stabilizing liquid (50 mmol/L of Tris-HCl buffer (pH: 7.5) including 0.5% by mass sucrose and 0.05% by mass sodium cholate) prepared in another vat and was left to stand for 30 minutes. After that, the nitrocellulose membrane was removed from the liquid and was dried at an environment of 25° C. for 24 hours.

A part to which the anti-influenza A-type antibody was immobilized corresponds to the inspection region including the second substance being bonded to the test substance, a part to which the anti-mouse IgG antibody was immobilized corresponds to the confirmation region including the substance bondable to the first substance, and a part to which the bromocresol green was immobilized corresponds to the amplification label region including the substance being reacted with the first amplification liquid.

(1-4) Production of Inspection Strip

The chromatographic carrier produced in (1-3) was attached to a back pressure-sensitive adhesion sheet (60 mm×300 mm (manufactured by Nippon Flour Mills Co., Ltd.)). Next, a 3 mm wide double-sided tape (NITTO DENKO CORPORATION) was fixed at a position 26 mm from the downstream side of the short side of the chromatographic carrier. Thereafter, the gold colloid-holding pad was fixed to the chromatographic carrier so that the downstream end of the double-sided tape overlaps the downstream end of the gold colloid antibody-holding pad produced in (1-2). The liquid-sending pad (a 25 mm×300 mm-cut glass fiber pad (Glass Fiber Conjugate Pad, manufactured by EMD Millipore Corporation) was attached to the upstream side of the chromatographic carrier so that the liquid-sending pad and the chromatographic carrier overlap with each other by 7 mm. The member produced in the above-described manner was cut using a guillotine-type cutter (CM4000, manufactured by Nippon Flour Mills Co., Ltd.)) parallel to a direction perpendicular to the long side (300 mm) so as to obtain a width of 5 mm, thereby producing 60 inspection strips (however, no absorption pad was included).

(1-5) Production of Amplification Liquid (1-5-1) Production of Amplification Liquid (Reducing Agent Solution) Sealed in Second Pot 23.6 mL of an aqueous solution of 1 mol/L of iron nitrate produced by dissolving iron (III) nitrate nonahydrate (manufactured by Wako Pure Chemical Industries, Ltd., 095-00995) in water and 13.1 g of citric acid (manufactured by Wako Pure Chemical Industries, Ltd., 038-06925) were dissolved in 290 g of water. Once the components were fully dissolved, 36 mL of nitric acid (10 weight %) solution was added thereto while stirring the solution using a stirrer, and 60.8 g of iron (II) ammonium sulfate hexahydrate (manufactured by Wako Pure Chemical Industries, Ltd., 091-00855) was added thereto. The solution thus prepared was used as a reducing agent solution which is a second amplification liquid sealed in the second pot.

(1-5-2) Production of Amplification Liquid (Silver Ion Solution) Sealed in First Pot 8 mL of a silver nitrate solution (including 10 g of silver nitrate) and 24 mL of an aqueous solution of 1 mol/L of iron nitrate were added to 66 g of water. Furthermore, this solution and a solution obtained by dissolving 5.9 mL of nitric acid (10 weight %), 0.1 g of dodecylamine (manufactured by Wako Pure Chemical Industries, Ltd., 123-00246), and 0.1 g of a surfactant $C_{12}H_{25}$—$C_6H_4$—O—$(CH_2CH_2O)_{50}H$ in 47.6 g of water in advance were mixed together, and this solution was used as a silver ion solution which is the first amplification liquid sealed in the first pot.

(1-6) Production of Absorption Pad

Sixty 12 mm×10 mm-cut glass fiber pads (glass filter paper, manufactured by Advantech Co., Ltd.) were prepared and was used as an absorption pad.

(1-7) Production of Components Of Immunochromatographic Kit

The lower case 20, the upper case 10, the intermediate member 30, the first pot 40, and the second pot 45 constituting the immunochromatographic kit 100 shown in FIG. 1 were respectively produced by injection molding using polypropylene as a material. The upper case was produced by injection molding using polypropylene containing 50% by mass of TAFTHREN (registered trademark) which is an olefinic elastomer manufactured by Sumitomo Chemical Co., Ltd. The upper case 10 has two deformable portions (first protrusive deforming portion and second protrusive deforming portion). These two deforming portions are not separated from the upper case 10, and all boundaries of the deforming portions are produced as a part of the upper case 10 by injection molding.

In the upper case of Example 1, the first protrusive deforming portion 12 shown in FIGS. 1 and 2 and the like has two protrusion portions, and the second protrusive deforming portion 14 has one protrusion portion. On the other hand, the upper case of Example 2 is configured to have two protrusive deforming portions having only one protrusion portion of the same shape as the second protrusive deforming portion 14 shown in FIGS. 1 and 2 and the like. That is, as shown in FIG. 8, the upper case of Example 2 has the first protrusive deforming portion 114 above the first pot 40 and has the second protrusive deforming portion 14 above the second pot 45. The modulus of elasticity in bending of the material of the upper case and the lower case were 90 (MPa) and 700 (MPa), respectively.

(1-8-1) Production of Immunochromatographic Kit of Example 1

The lower case 20, the inspection strip 1 produced in (1-4), and the absorption pad 6 produced in (1-6) were fixed as illustrated in FIGS. 1 and 2. Next, each of the first pot 40 and the second pot 45 was filled with the amplification liquid 41 to be sealed in the first pot 40 prepared in (1-5-2) and the amplification liquid 46 to be sealed in the second pot 45 prepared in (1-5-1), respectively. The pot 45 was sealed with aluminum foil as the sheet member 48, and the pot 40 was sealed with aluminum foil as the sheet member 43, respectively. As shown in FIGS. 1 and 2, the second pot 45 was attached to the lower case 20 with the sheet member 48 facing upward and the first pot 40 was attached to the intermediate member 30 with the sheet member 43 facing downward. In a state where the upper case 10 and the lower case 20 were fitted so that the outer peripheries thereof came in contact with each other, contact portions between the upper case and the lower case were joined by ultrasonic welding. At this time, it was confirmed that in welded portions, all portions were uniformly welded in a sealed state. In this manner, the immunochromatographic kit of Example 1 was produced.

(1-8-2) Production of Immunochromatographic Kit of Example 2

An immunochromatographic kit of Example 2 was produced in the same manner as in the immunochromatographic kit of Example 1 except that an upper case different in the shape of the first protrusive deforming portion from that of Example 1 was used.

(2) Evaluation (2-1) Spotting

A liquid was produced by diluting simulated positive specimen (BD Flu examine control A+B (manufactured by Becton, Dickinson and Company)) using an extraction liquid (1% by mass BIGCHAP-containing 1% BSA-PBS) 2,560 times, and 40 μL of the liquid was attached in a scattered manner to the anti-influenza A-type antibody-modified gold colloid-holding pad.

(2-2) Deployment of Amplification Liquid (Reducing Agent Solution) Sealed in Second Pot Immediately after spotting the specimen liquid of (2-1), by pressing down the second protrusive deforming portion 14, the aluminum foil which is the sheet member 48 sealing the second amplification liquid 46 sealed in the second pot 45 was torn up, and by allowing the liquid-sending pad 4 to be immersed into the second pot 45, the second amplification liquid 46 was supplied to the insoluble carrier 2 using capillarity.

(2-3) Silver Amplification

After the discoloration of the amplification label region $L_3$ from green to orange, the first protrusive deforming portion 12 (first protrusive deforming portion 114 in Example 2) was pressed down to move the first pot 40 toward the tearing portion 34 of the first pot accommodation portion 32 of the intermediate member 30, thereby allowing the tearing portion 34 to press down and tear the aluminum foil which is the sheet member 43 sealing the first pot 40. The silver ion solution that is the first amplification liquid 41 was supplied to the insoluble carrier 2 from the opening portion of the intermediate member 30, and therefore silver amplification reaction was performed. The silver amplification reaction was completed in tens of seconds.

(2-4) Calculation of Concentration Value of Inspection Region

Concentrations in the inspection region $L_1$ and the confirmation region $L_2$ of the immunochromatographic kits of Examples 1 and 2 after the amplification treatment were visually observed. Furthermore, the chromatographic carriers were taken out from the immunochromatographic kits of Examples 1 and 2, the concentration of the inspection region $L_1$ was captured using LAS4000 (manufactured by Fujifilm Corporation), and therefore a concentration difference (ΔOD=(the concentration of the inspection region $L_1$)−(the concentration of a background portion)) was calculated. A case where ΔOD≥0.015 can be said that the amplification results are generally good.

(2-5) Measurement of Supplying Amount of Silver Ion Solution

A change in weight of the first pot before and after pressing the first protrusive deforming portion was measured and a supplying amount of the first amplification liquid was obtained based on the following calculation.

(first amplification liquid supply amount)=((weight of first pot before pressing first protrusive deforming portion)−(weight of first pot after pressing first protrusive deforming portion))/(specific weight of silver ion solution)

A value in which a supplying amount of the first amplification liquid (silver ion solution) was 40 μL or more was set as a target amount.

The evaluation results are shown in Table 1. Table 1 shows the results of repeating the same test 5 times for each example. A supply amount of the silver ion solution was determined according to the following criteria.

A: 40 μL or more

B: 20 μL or more and less than 40 μL

C: Less than 20 μL

ΔOD was determined according to the following criteria.

A: 0.05 or more

B: 0.015 or more and less than 0.05

C: less than 0.015.

Practical determination of the above determination results is shown below.

A: It is possible to perform amplification with high accuracy and sufficient analysis is possible.

B: Although the accuracy of amplification deteriorates, the performance is within an acceptable range.

C: Amplification performance is not exerted sufficiently, and the performance is not acceptable.

In Table 1, the results in which a degree of inclination of the first pot which was moved by deforming the first protrusive deforming portion was visually confirmed are also described. A case in which the first pot was pressed in a plane without incline, was evaluated as "pressed in a plane", and a case in which the first pot after the movement was inclined, was evaluated as "inclined".

TABLE 1

| | Experiment N | Supplying amount of silver ion solution [μl] | Determination | ΔOD | Determination | ΔOD CV of N5 | Pressed manner of first pot | Practical determination |
|---|---|---|---|---|---|---|---|---|
| Example 1 | 1 | 71 | A | 0.076 | A | 9.7% | Pressed in a plane | A |
| | 2 | 79 | A | 0.094 | A | | Pressed in a plane | A |
| | 3 | 81 | A | 0.084 | A | | Pressed in a plane | A |
| | 4 | 83 | A | 0.077 | A | | Pressed in a plane | A |
| | 5 | 74 | A | 0.076 | A | | Pressed in a plane | A |
| Example 2 | 1 | 30 | B | 0.031 | B | 41% | Slightly inclined | B |
| | 2 | 74 | A | 0.076 | A | | Slightly inclined | A |
| | 3 | 40 | A | 0.084 | A | | Slightly inclined | A |
| | 4 | 35 | B | 0.036 | B | | Slightly inclined | B |
| | 5 | 71 | A | 0.067 | A | | Slightly | A |

Based on Table 1, it is clear that in any immunochromatographic kit of Examples 1 and 2, the supply amount of the first amplification liquid and the value of ΔOD were both within an acceptable range, and thus sufficient amplification was possible. In particular, in Example 1 where the number of protrusions of the first protrusive deforming portion pressing the first pot 40 was two, it was possible to press the first pot 40 in a plane and to stably supply a target amount or more of the silver ion solution, and thus the amplification reaction could be stably and successfully carried out. Therefore, it could be confirmed that the coefficient of variation CV of ΔOD of Example 1 was about 10%, which was good, and that it was possible to accurately perform measurement with the aspect having two protrusion portions.

In addition, the measurement result of ΔOD in the table corresponded with the evaluation result in the case of visual evaluation, and it was confirmed that, without using a device using a power source such as an analyzer, the immunochromatographic kit which can supply a solution necessary for realizing high sensitivity, such as an amplification liquid, is provided so as to be used in an experiment, and therefore analysis evaluation is possible.

EXPLANATION OF REFERENCES

1: inspection strip
2: insoluble carrier
3: label-holding pad
4: liquid-sending pad
6: absorption pad
7: back pressure-sensitive adhesion sheet
9: housing case
10: upper case
12: first protrusive deforming portion
12a: top of first protrusive deforming portion
12b: protrusion portion of first protrusive deforming portion
12c: inclined surface of first protrusive deforming portion
14: second protrusive deforming portion
14a: top of second protrusive deforming portion
14b: protrusion portion of second protrusive deforming portion
16: hole for dropwise addition of specimen liquid
18: observation window
20: lower case
21: insoluble carrier accommodation portion
22: absorption pad accommodation portion
24: second pot accommodation portion
30: intermediate member
32: first pot accommodation portion
34: tearing portion
35: flow path-forming member
36: rear surface of flow path-forming member 35
40: first pot for first amplification liquid
41: first amplification liquid
42: pot container
43: sheet member
45: second pot for second amplification liquid
46: second amplification liquid
47: pot container
48: sheet member
100: immunochromatographic kit
114: protrusive deforming portion
114a: top of protrusive deforming portion 114
114b: protrusion portion of protrusive deforming portion 114

What is claimed is:

1. An immunochromatographic kit for detecting a test substance in a specimen liquid, the kit comprising:
    an inspection strip including an insoluble carrier that deploys the specimen liquid and has an inspection region for the test substance;
    a first pot and a second pot, each including a surface having a sheet member, a first amplification liquid and a second amplification liquid being sealed, respectively, in the first pot and the second pot in order to amplify a detection signal in the inspection region; and a housing case that includes the inspection strip, the first pot, and the second pot, wherein:

the housing case includes a lower case having an accommodation portion in which the inspection strip is disposed, an upper case joined to the lower case along a peripheral edge thereof, and an intermediate member disposed between the upper case and the lower case, the intermediate member includes a tearing portion that tears the sheet member of the first pot, the tearing portion facing the sheet member of the first pot, the upper case includes, at a part facing the first pot, a first protrusive deforming portion that deforms towards a side of the first pot when applied with pressing force from outside, whereby the tearing portion of the intermediate member tears the sheet member of the first pot, and the upper case includes, at a part facing the second pot, a second protrusive deforming portion that deforms towards a side of the second pot when applied with pressing force from outside, so that the sheet member of the second pot is torn, due to the first protrusive deforming portion being applied with the pressing force, the first pot is moved to a position at which the sheet member of the first pot is torn by the tearing portion of the intermediate member, the first protrusive deforming portion includes two protrusion portions that project towards the first pot side and that come into contact with the first pot so as to move the first pot in a case in which pressing force is applied to the first protrusive deforming portion, and the two protrusion portions of the first protrusive deforming portion are disposed such that distal ends of the two protrusion portions respectively come into contact with the first pot so as to move the first pot while the distal ends are respectively gradually displaced towards the end sides of the first pot.

2. The immunochromatographic kit according to claim 1, wherein the first protrusive deforming portion has a centrally symmetrical protruding shape.

3. The immunochromatographic kit according to claim 2, wherein the two protrusion portions are disposed symmetrically with respect to a top of the protruding shape.

4. The immunochromatographic kit according to claim 2, wherein the two protrusion portions are independently formed at inclined surfaces that sandwich the top of the protruding shape therebetween.

5. The immunochromatographic kit according to claim 1, wherein the two protrusion portions are disposed symmetrically with respect to a center of a contact surface of the first pot.

6. The immunochromatographic kit according to claim 5, wherein the two protrusion portions are disposed closer to an end side than a half of a distance from a center to an end of the contact surface of the first pot.

7. The immunochromatographic kit according to claim 1, wherein a material forming the first protrusive deforming portion has a modulus of elasticity in bending of 50 MPa to 350 MPa.

8. The immunochromatographic kit according to claim 1, wherein:
a material forming the upper case has a modulus of elasticity in bending of 50 MPa to 350 MPa, and
a material forming the lower case has a modulus of elasticity in bending of 500 MPa to 900 MPa.

9. The immunochromatographic kit according to claim 1, wherein the upper case is integrally formed with the first protrusive deforming portion and the second protrusive deforming portion by injection molding.

\* \* \* \* \*